United States Patent
Sato et al.

(10) Patent No.: US 6,333,441 B1
(45) Date of Patent: *Dec. 25, 2001

(54) PREPARATION OF CIS—OLEFINS

(75) Inventors: Fumie Sato, 1-219, Kugenumahigashi 3-chome, Fujisawa-shi, Kanagawa-ken; Katsuaki Miyaji, Funabashi; Takehiro Amano, Tokyo, all of (JP)

(73) Assignees: Nissan Chemical Industries, Ltd., Tokyo; Fumie Sato, Kanagawa-ken, both of (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/026,681

(22) Filed: Mar. 4, 1993

(30) Foreign Application Priority Data

Mar. 9, 1992 (JP) ..................................................... 4-085952

(51) Int. Cl.⁷ .............................. C07C 5/05; C07C 39/00; C07C 27/04; C07C 29/00
(52) U.S. Cl. ........................... 585/273; 585/266; 585/271; 585/275; 585/277; 568/780; 568/876; 568/828; 568/903; 568/857; 568/880; 568/881; 560/1; 562/405; 562/463; 562/512
(58) Field of Search .................................... 568/780, 876, 568/828, 903, 857, 880, 881; 562/405, 463, 512; 560/1, 4; 585/266, 271, 273, 275, 277

(56) References Cited

U.S. PATENT DOCUMENTS 3,715,404 * 2/1973 Lindlar et al. ........................ 568/876
3,932,547 * 1/1976 Mertweiller et al. ................. 568/876
4,177,220 * 12/1979 Nozaki .................................. 585/514
4,238,358 * 12/1980 Holy et al. ............................ 568/876
4,388,479 * 6/1983 Gryaznov et al. .................... 568/828

OTHER PUBLICATIONS

Weir, J.R. et al, Journal of Organic Chemistry, (1980), vol. 45, No. 24, pp. 4926–4931.

Cortese et al, Journal of Organic Chemistry, (1978), vol. 43, No. 20, pp. 3985–3987.

Barley M. Trost, Tetrahedron Letters, vol. 30, No. 35, pp. 4657–4660, 1989.

The Palladium—Tribuiyiammonium Formate Reagent in the Siereoselective Hydrogenation, and Siereo–and Regioselective Hydroarylation of Alkyl 4–Hydroxy-2–Alkynoates: a Route to Substituted Butenolides, A. Arcadi et al, Tetrahedron vol. 44, No. 2, pp. 481–490, 1988.

* cited by examiner

Primary Examiner—Elizabeth D. Wood
(74) Attorney, Agent, or Firm—Birch, Stewart, Kolasch & Birch, LLP

(57) ABSTRACT

A cis-olefin of the formula: $R_1$—CH═CH—$R_2$ is prepared by reducing an alkyne of the formula: $R_1$—C≡C—$R_2$ with formic acid in the presence of a palladium catalyst. $R_1$ and $R_2$ are independently selected from the group consisting of a hydrogen atom, ester group, substituted silyl group, carboxyl group, cyano group, aliphatic C1–C20 hydrocarbon group, and phenyl group. The cis-olefin which is a useful intermediate for the synthesis of fine chemicals is selectively produced in high yields.

7 Claims, No Drawings

PREPARATION OF CIS— OLEFINS

FIELD OF THE INVENTION

This invention relates to the preparation of cis-olefins, and more particularly, a method for preparing cis-olefins through formic acid reduction of alkynes in the presence of palladium catalysts.

BACKGROUND OF THE INVENTION

Cis-olefins are useful intermediates for the synthesis of many fine chemicals, especially for the synthesis of bioactive materials having a double bond cis-conformed in their structural formula.

In the prior art, cis-olefins were prepared by the hydrogen reduction of alkynes using Lindlar catalysts. Also known in the art are silicon hydride reduction using palladium catalysts (Barley M. Trost, Tetrahedron Letters, Vol. 30, No. 35 pp. 4657, 1989).

These method have several drawbacks. The hydrogen reduction method using Lindlar catalysts is difficult to obtain cis-olefins of high purity since trans-olefins and saturated compounds are by-produced in addition to the desired cis-olefins. The hydrogen reduction method has the danger of a fire. The silicon hydride reduction method must use expensive silicon hydrides and is generally low in cis-olefin selectivity so that trans-olefins can be a major product.

In Tetrahedron, Vol. 44, pp. 481, 1988, A. Arcadi et al discloses formic acid reduction in which aryl iodides are reacted with alkyl 4-hydroxy-2-alkynoates and in the presence of formic acid, tri-n-butylamine and a palladium (II) catalyst.

However, the above formic acid reduction method only provides cyclic product as shown below. No cis-olefins which are pure hydrogenated products are available.

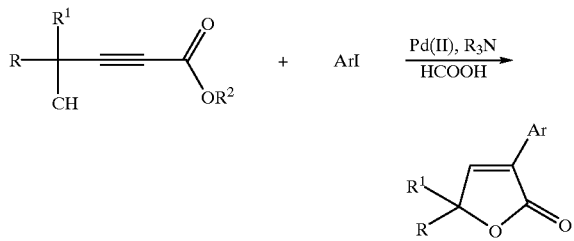

There is a need to have a simple method capable of selectively producing cis-olefins in high yields.

SUMMARY OF THE INVENTION

Therefore, an object of the present invention is to provide a method for selectively preparing cis-olefins without substantial formation of trans-olefins and saturated compounds.

The present invention is addressed to a method for preparing a cis-olefin of the following general formula (2):

wherein $R_1$ and $R_2$ are independently selected from the group consisting of a hydrogen atom, ester group, substituted silyl group, carboxyl group, cyano group, substituted or unsubstituted aliphatic hydrocarbon group having 1 to 20 carbon atoms, and substituted or unsubstituted phenyl group. The method is characterized by reducing an alkyne of the following general formula (1):

$$R_1\text{—}C\equiv C\text{—}R_2 \tag{1}$$

wherein $R_1$ and $R_2$ are as defined above with formic acid in the presence of a palladium catalyst.

DETAILED DESCRIPTION OF THE INVENTION

The method of the invention starts with an alkyne of formula (1).

$$R_1\text{—}C\equiv C\text{—}R_2 \tag{1}$$

In formula (1), $R_1$ and $R_2$, which may be identical or different, are independently selected from the group consisting of (a) a hydrogen atom, (b) an ester group, (c) a substituted silyl group, (d) a carboxyl group, (e) a cyano group, (f) a substituted or unsubstituted aliphatic hydrocarbon group having 1 to 20 carbon atoms, and (g) a substituted or unsubstituted phenyl group. Examples of the group represented by $R_1$ and $R_2$ are given below.

Examples of (b) ester group include substituted or unsubstituted alkoxycarbonyl groups having 1 to 10 carbon atoms and substituted or unsubstituted phenoxycarbonyl groups. The substituted or unsubstituted alkoxycarbonyl groups having 1 to 10 carbon atoms include methoxycarbonyl, ethoxycarbonyl, n-propoxycarbonyl, i-propoxycarbonyl, n-butoxycarbonyl, sec-butoxycarbonyl, t-butoxycarbonyl, pentoxycarbonyl, hexoxycarbonyl, heptoxycarbonyl, octoxycarbonyl, nonanoxycarbonyl, decisoxycarbonyl, methoxymethoxycarbonyl, methylthiomethoxycarbonyl, tetrahydropyranoxycarbonyl, tetrahydrofuranotoxycarbonyl, benzyloxymethoxycarbonyl, phenasiloxycarbonyl, o-methylphenoxymethoxycarbonyl, m-methylphenoxymethoxycarbonyl, p-methylphenoxymethoxycarbonyl, o-bromophenasiloxycarbonyl, m-bromophenasiloxycarbonyl, p-bromophenasiloxycarbonyl, bezyloxycarbonyl, o-methylphenasiloxycarbonyl, m-methylphenasiloxycarbonyl, p-methylphenasiloxycarbonyl, 2,2,2-trichloroethoxycarbonyl, 2-chloroethoxycarbonyl, 2-methylthioethoxycarbonyl, cyclopentyloxycarbonyl, cyclohexyloxycarbonyl, allyloxycarbonyl groups, etc. The substituted or unsubstituted phenoxycarbonyl groups include biphenoxycarbonyl, 4-(4-fluorophenyl) phenoxycarbonyl, 4-(4-chlorophenyl)phenoxycarbonyl, 4-(4-bromophenyl)phenoxycarbonyl, 4-(4-iodophenyl) phenoxycarbonyl groups, etc.

Examples of (c) substituted silyl group include trimethylsilyl, i-propyldimethylsilyl, t-butyldimethylsilyl groups, etc.

Examples of (f) unsubstituted aliphatic hydrocarbon group having 1 to 20 carbon atoms include methyl, ethyl, n-propyl, i-propyl, n-butyl, i-butyl, sec-butyl, t-butyl, n-amyl, i-amyl, hexyl, heptyl, octyl, nonyl, decyl, undecyl, dodecyl, tridecyl, hexadecyl, octadecyl, eicosyl groups, etc.

The substituents on (f) aliphatic hydrocarbon groups and (g) phenyl group include hydroxyl, protected hydroxyl, halogen, formyl, ester, carbonyl, amide, carboxyl, cyano, p-methylthio, phenyl, fluorophenyl, chlorophenyl, bromophenyl, and iodophenyl groups.

By the protected hydroxyl groups are meant those hydroxyl groups protected with substituted silyl groups such as trimethylsilyl and t-butyldimethylsilyl groups, alkoxy-alkyl groups such as methoxymethyl and ethoxymethyl groups, acyl groups such as acetyl and benzoyl groups, trityl, tetrahydropyranyl, benzyl and p-chlorobenzyl groups.

The ester substituents include substituted or unsubstituted alkoxycarbonyl groups having 1 to 10 carbon atoms and substituted or unsubstituted phenoxycarbonyl groups as mentioned for (b).

The halogen substituents include fluorine, chlorine, bromine and iodine atoms.

The amide substituents include substituted or unsubstituted alkoxycarbonylamide groups having 1 to 10 carbon atoms and substituted or unsubstituted phenoxycaronylamide groups. The substituted or unsubstituted alkoxycarbonylamide groups having 1 to 10 carbon atoms include methoxycarbonylamino, ethoxycarbonylamino, n-propoxycarbonylamino, i-propoxycarbonylamino, n-butoxycarbonylamino, sec-butoxycarbonylamino, t-butoxycarbonylamino, pentoxycarbonylamino, hexoxycarbonylamino, heptoxycarbonylamino, octoxycarbonylamino, nonanoxycarbonylamino, decisoxycarbonylamino, methoxymethoxycarbonylamino, methylthiomethoxycarbonylamino, tetrahydropyranoxycarbonylamino, tetrahydrofuranotoxycarbonylamino, benzyloxymethoxycarbonylamino, phenasiloxycarbonylamino, o-methylphenoxymethoxycarbonylamino, m-methylphenoxymethoxycarbonylamino, p-methylphenoxymethoxycarbonylamino, o-bromophenasiloxycarbonylamino, m-bromophenasiloxycarbonylamino, p-bromophenasiloxycarbonylamino, benzyloxycarbonylamino, o-methylphenasiloxycarbonylamino, m-methylphenasiloxycarbonylamino, p-methylphenasiloxycarbonylamino, 2,2,2-trichloroethoxycarbonylamino, 2-chloroethoxycarbonylamino, 2-methylthioethoxycarbonylamino, cyclopentyloxycarbonylamino, cyclohexyloxycarbonylamino, allyloxycarbonylamino groups, etc. The amide moiety of the alkoxycarbonylamide and phenoxycarbonylamide groups may have a substituent which is selected from the above-mentioned substituents on the C1–C10 aliphatic hydrocarbon and phenyl groups and which may further have a substituent such as a hydroxyl, protected hydroxyl, halogen, formyl, ester, amide, carboxyl, cyano, p-methylthio, phenyl, fluorophenyl, chlorophenyl, bromophenyl, and iodophenyl group.

Illustrative, non-limiting examples of the alkyne of formula (1) include 1-decyne, 1-hydroxy-4-heptyne, 1-hydroxy-2-octyne, 3-hydroxy-1-octyne, 3-hydroxy-4-decyne, 2-hydroxy-2-methyl-3-nonyne, 1-trimethylsilyl-1-heptyne, 1-t-butyldimethylsiloxy-2-octyne, 1-trimethylsilyl-3-hydroxy-1-octyne, 1-carboxy-3-hexyne, 1-carboxy-1-heptyne, 1-methoxycarbonyl-1-heptyne, 1-ethoxycarbonyl-4-heptyne, 1-allyloxycarbonyl-1-heptyne, 1-methoxycarbonyl-6-hydroxy-4-hexyne, 1-ethoxycarbonyl-3-hexyne, 3-oxy-4-decyne, 2-oxo-5-octyne, 1-benzyloxy-2-octyne, 1-tetrahydropyranoxy-2-octyne, 1-formyl-3-hexyne, 1-bromo-4-heptyne, 1-cyano-4-heptyne, phenylacetylene, 1-phenyl-1-butyne, and 1-phenylthio-4-heptyne.

According to the present invention, these alkynes are reduced with formic acid in the presence of palladium catalysts. The palladium catalysts used herein may be complexes of palladium having a valence of zero or plus two.

Examples of the palladium catalyst include $Pd(PPh_3)_4$, $Pd(Ph^tBu_2)_2$, $Pd(P^tBu_3)_2$, $Pd[P(c-C_6H_{11})_3]_2$, $Pd[P(OPh)_3]_4$, $Pd[P(OEt)_3]_4$, $Pd(AsPh_3)_4$, $Pd(CO)(PPh_3)_3$, $Pd(PPh_3)_2(CH_2=CH_2)$, $Pd(PPh_3)_2(CF_2=CF_2)$, $Pd[P(c-C_6H_{11})_3]_2(CH_2=CH_2)$, $Pd[P(c-C_6H_{11})_3]_2(CF_2=CF_2)$, $Pd(PBu_3)_2(CH_2=CH_2)$, $Pd(PPh_3)_2(CF_2=CF_2)$, $Pd[P(OC_6H_4CH_3\text{-}o)]_2(CH_2=CH_2)$, $Pd(PPh_3)_2(CH_3OOCCH=CHCOOCH_3)$, $Pd[P(OPh)_3]_2(CH_3OOCCH=CHCOOCH_3)$, $Pd(PPh_3)_2(NCCH=CHCN)$, $Pd[P(OPh)_3]_2(NCCH=CHCN)$, $Pd(PPh_2Me)_2(PhCH=CH_2)$, $Pd(PPh_2Me)_2(CH_2=CHCOOMe)$, $Pd(PPh_2Me)_2[CH_2=CH(CH_3)CN]$, $Pd(PPh_2Me)_2[CH_2=CH(CH_3)COMe]$, $Pd(1,5-C_8H_{12})_2$, $Pd_2(DBA)_3$, $Pd_3(CO)_3(P^tBu_3)_3$, $Pd_3(2,6-Me_2C_6H_3NC)_6$, $PdCl(CH_3)(COD)$, $Pd(CH_3)_2(PEt_3)_2$, $Pd(C_2H_5)_2(PMe_2Ph)_2$, $Pd(CH_3)_2(DPPE)$, $Pd(CH_3)(PPh_3)_2$, $PdPh_2(PEt_3)_2$, $Pd(CH_2Ph)_2(DMPE)$, $Pd(CH_2Ph)_2(PMe_3)_2$, $Pd(CH_3)Cl(PEt_3)_2$, $Pd(CH_3)I(PMe_3)_2$, $Pd(CH_3)Br(PEt_3)_2$, $PdI(Ph)(PMe_3)_2$, $Pd(COPh)Cl(PMe_3)_2$, $Pd(COMe)I(PMe_3Ph_2)_2$, $Pd(COMe)Cl(PPh_3)_2$, $Pd(COEt)Cl[P(OMe_3)]_2$, $PdI(Ph)(PMe_2Ph)_2$, $Pd(CH\equiv CH)_2(PEt_3)_2$, $Pd(PhC\equiv C)Cl(PBu_3)_2$, $Pd(Me_3CCH_2)_2(BPY)$, $Pd(C_5H_6)Ph(PEt_3)$, $Pd(\eta\text{-}C_3H_5)(C_5Me_5)$, $[Pd(\eta\text{-}C_3H_5)(COD)]BF_4$, $[PdCl(1,1-Me_2-C_3H_5)]_2$, $Pd_2(DBA)_3CHCl_3$, $Pd(DBA)_2$, $PdCl_2(MeCN)_2$, $PdCl_2(PhCN)_2$, $Li_2PdCl_4$, $Na_2PdCl_4$, $[Pd(MeCN)_4](BF_4)_2$, $[Pd(\eta\text{-}C_3H_5)Cl]_2$, $Pd(\eta\text{-}C_3H_5)_2$ and $Pd(OAc)_2$.

Note that DBA is dibenzylideneacetone, COD is cyclooctadiene, DPPE is diphenylphosphinethane, DMPE is dimethylphosphinethane, and BPY is dipyridyl.

The palladium catalyst is generally used in an amount of about 0.1 to 100 mol %, preferably about 1 to 10 mol % based on the moles of the alkyne of formula (1).

Formic acid is generally used in an amount of about 1 to 1000 mol %, preferably about 10 to 500 mol % based on the moles of the alkyne of formula (1).

To the reaction system may be added a compound selected from the group consisting of amines, phosphines and phosphites.

The amines used herein are of the following general formulae (3) to (5), the phosphines are of the following general formula (6), and the phosphites are of the following general formula (7).

(3)

$R_3NH_2$

(4)

$R_3$
  \
   NH
  /
$R_5$ (5)

$R_3$
  \
$R_4$—N
  /
$R_5$

(6)

$R_6$
  \
$R_7$—P
  /
$R_8$

(7)

$R_6O$
  \
$R_7O$—P
  /
$R_8O$

In these formulae, $R_3$, $R_4$, $R_5$, $R_6$, $R_7$, and $R_8$ are independently hydrocarbon groups having 1 to 10 carbon atoms, for example, methyl, ethyl, n-propyl, i-propyl, n-butyl, i-butyl, sec-butyl, t-butyl, n-amyl, i-amyl, hexyl, heptyl, octyl, nonyl, decyl, benzyl, and phenyl groups.

Preferably, the amines are added in amounts of about 0.1 to 10 equivalents, more preferably about 0.5 to 5 equivalents per equivalent of the alkyne of formula (1). Also the phosphines or phosphites are preferably added in amounts of about 0.1 to 100 mol %, more preferably about 1 to 30 mol % based on the moles of the alkyne of formula (1).

In the practice of the invention, reduction may be carried out in a suitable solvent, such as ether, hydrocarbon, ester, amide, and sulfoxide solvents. Suitable ether solvents are diethyl ether, di-n-propyl ether, di-i-propyl ether, tetrahydrofuran, and 1,4-dioxane. Suitable hydrocarbon solvents are n-pentane, i-pentane, n-hexane, benzene, toluene, and xylene. Suitable ester solvents are methyl acetate, ethyl acetate, n-propyl acetate, and i-propyl acetate. Suitable amide solvents are dimethylformamide and dimethylacetamide. A suitable sulfoxide solvent is dimethylsulfoxide. These solvents may be used alone or in admixture of two or more.

The reducing temperature generally ranges from about $-40°$ C. to the reflux temperature of the solvent, preferably from about $-10°$ C. to about $60°$ C. The reaction time is generally about ½ to about 12 hours.

By reducing the alkyne of formula (1) with formic acid in the presence of a palladium catalyst under the above-mentioned conditions, a cis-olefin of formula (2) is selectively obtained in high yields while the formation of trans-olefins and saturated compounds is substantially nil.

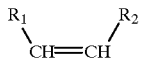

In formula (2), $R_1$ and $R_2$ are as defined above.

There has been described a method for readily preparing cis-olefins of formula (2) from alkynes of formula (1) under moderate conditions, the cis-olefins being useful intermediates for the synthesis of fine chemicals.

EXAMPLE

Examples of the present invention are given below by way of illustration and not by way of limitation.

Example 1

In 50 ml of tetrahydrofuran was dissolved 20.9 ml (150% mmol) of triethylamine. To the solution were added 6.38 grams of formic acid in water (concentration 88% by weight), 1.29 grams (1.25 mmol) of Pd(DBA)$_3$·CHCl$_3$, and 1.25 ml (5 mmol) of n-tributylphosphine. The mixture was agitated for 10 minutes at room temperature. To the solution was added dropwise a solution containing 12.0 grams (79 mmol) of 2-undecyne in 150 ml of tetrahydrofuran. The mixture was agitated for two hours at 40° C.

At the end of reaction, 50 ml of a saturated ammonium chloride aqueous solution and 100 ml of n-hexane were added to the reaction solution. The organic layer was extracted, dried over magnesium sulfate, and filtered. By distilling off the solvent, there was obtained 12 grams of 2-undecene in a substantially quantitative yield.

The result of gas chromatography revealed that the cis-undecene was at least 99% pure and formation of trans-undecene and undecane was less than 1% for each.

The analytical results of the product are shown below.

H NMR (CDCl$_3$, 300 MHz) δ0.87 (t, J=5.9 Hz, 3H), 1.20~1.40 (m, 12H), 1.60 (d, J=5.0 Hz, 3H), 1.95~2.08 (m, 2H), 5.32~5.50 (m, 2H)

$^{13}$C NMR (CDCl$_3$, 75 MHz) δ130.9, 123.6, 31.9, 29.7, 29.6, 29.3, 26.9, 22.7, 14.1

Examples 2–13

The procedure of Example 1 was repeated except that the starting alkyne and the reaction time were changed as shown in Table 1. The reaction scheme is shown below.

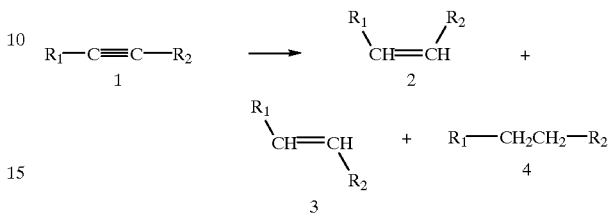

TABLE 1

| Example | Alkyne (1) | Reaction time, hr. | Selectivity, % (2) | (3) | (4) | Yield (%) |
|---------|------------|--------------------|--------------------|-----|-----|-----------|
| 2 | 1-decyne | 1 | 98 | — | 2 | 65 |
| 3 | 1-methoxycarbonyl-1-heptyne | 2 | 98 | 2 | 0 | 95 |
| 4 | 1-phenyl-1-butyne | 3 | 89 | 5 | 6 | 100 |
| 5 | 1-hydroxy-2-octyne | 1.5 | 99 | 0 | 1 | 91 |
| 6 | 3-hydroxy-4-decyne | 3 | >99 | <1 | <1 | 90 |
| 7 | phenylacetylene | 3 | >99 | — | <1 | 70 |
| 8 | 1-carboxy-1-heptyne | 3 | >99 | <1 | <1 | 100 |
| 9 | 3-acetoxy-4-decyne | 3 | >99 | <1 | <1 | 100 |
| 10 | 2-hydroxy-2-methyl-3-octyne | 3 | >99 | <1 | <1 | 100 |
| 11 | 1-t-butyldimethyl-silyloxy-2-octyne | 3 | >99 | <1 | <1 | 100 |
| 12 | 1-tetrahydropyranoxy-2-octyne | 3 | >99 | <1 | <1 | 100 |
| 13 | 1-ethoxycarbonyl-3-hexyne | 3 | >99 | <1 | <1 | 100 |

The analytical data of products (2) are shown below.

Example 2

H NMR (CCl$_4$, 90 MHz) δ0.70~1.00 (m, 3H), 1.10~1.50 (m, 12H), 1.80~2.05 (m, 2H), 4.68~4.98 (m, 2H), 5.63 (ddt, J=6.9, 10.4, 18.0 Hz, 1H)

Example 3

H NMR (CDl$_3$, 300 MHz) δ0.89 (t, J=6.5 Hz, 3H), 1.21~1.62 (m, 6H), 2.65 (dt, J=7.4, 7.2 Hz, 2H), 3.71 (s, 3H), 5.77 (d, J=11.5 Hz, 1H), 6.24 (dt, J=11.5, 7.5 Hz, 1H)

Example 4

H NMR (CCl$_4$, 90 MHz) δ1.00 (t, J=7.9 Hz, 3H), 2.25~2.65 (m, 2H), 5.48 (dt, J=7.9, 12.5 Hz, 1H), 6.25 (d, J=12.5 Hz, 1H), 7.00~7.25 (m, 5H)

Example 5

H NMR (CDl$_3$, 300 MHz) δ0.89 (t, J=6.6 Hz, 3H), 1.15~1.50 (m, 6H), 1.88 (brs, 1H), 2.06 (dt, J=6.9, 6.9 Hz, 2H), 4.19 (d, J=5.8 Hz, 2H), 5.47~5.70 (m, 2H)

$^{13}$C NMR (CDCl$_3$, 75 MHz) δ133.0, 128.3, 58.4, 31.3, 29.2, 27.3, 22.5, 14.0

Example 6

H NMR (CDCl$_3$, 300 MHz) δ0.78~1.00 (m, 6H), 1.20~1.70 (m, 9H), 1.95~2.18 (m, 2H), 4.25~4.42 (m, 1H), 5.27~5.40 (m, 1H), 5.51 (dt. J=7.3, 10.9 Hz, 1H), $^{13}$C NMR (CDCl$_3$, 75 MHz) δ132.6, 132.2, 69.0, 31.4, 30.3, 29.4, 27.7, 22.5, 14.0, 9.7

Example 7

H NMR (CCl$_4$, 90 MHz) δ5.04 (dd, J=1.5, 11.5 Hz, 1H), 5.54 (dd, J=1.5, 18.0 Hz, 1H), 6.53 (dd, J=11.5, 18.0 Hz, 1H), 6.98~7.30 (m, 5H)

Example 8

H NMR (CDCl$_3$, 300 MHz) δ0.89 (t, J=6.1 Hz, 3H), 1.20~1.60 (m, 6H), 2.60~2.71 (m, 2H), 5.79 (d, J=11.5 Hz, 1H), 6.36 (dt, J=7.5, 11.5 Hz, 1H)

Example 9

H NMR (CDCl$_3$, 300 MHz) δ0.75~1.00 (m, 6H), 1.18~1.43 (m, 6H), 1.43~1.73 (m, 2H), 2.03 (s, 3H), 2.05~2.22 (m, 2H), 5.22~5.34 (m, 1H), 5.40~5.61 (m, 2H)
$^{13}$C NMR (CDCl$_3$, 75 MHz) δ170.4, 134.4, 127.7, 71.6, 31.4, 29.2, 27.8, 27.7, 22.5, 21.3, 14.0, 9.4

Example 10

H NMR (CDCl$_3$, 300 MHz) δ0.89 (t, J=6.4 Hz, 3H), 1.37 (s, 6H), 1.15~1.65 (m, 6H), 2.31 (dt, J=6.9, 6.5 Hz, 2H), 5.31 (dt, J=11.8, 7.3 Hz, 1H), 5.48 (d, J=11.8 Hz, 1H)
$^{13}$C NMR (CDCl$_3$, 75 MHz) δ136.6, 131.4, 71.6, 31.6, 31.1, 29.7, 28.0, 22.6, 14.0

Example 11

H NMR (CDCl$_3$, 300 MHz) δ0.12 (s, 6H), 0.98 (s, 9H), 0.80~1.06 (m, 3H), 1.20~1.53 (m, 6H), 1.93~2.13 (m, 2H), 4.13 (d, J=4.5 Hz, 2H), 5.13~5.60 (m, 2H)

Example 12

H NMR (CDCl$_3$, 300 MHz) δ0.88 (t, J=7.1 Hz, 3H), 1.20~1.95 (m, 12H), 2.08 (d t, J=7.1, 6.6 Hz, 2H), 3.45~3.59 (m, 1H), 3.82~3.96 (m, 1H), 4.07 and 4.2 6 (2dd, J=5.9, 12.2 Hz and 4.9, 12.2 Hz, 2H), 4.64 (brs, 1H), 5.50~5.65 (m, 2H)
$^{13}$C NMR (CDCl$_3$, 75 MHz) δ133.8, 125.6, 97.8, 62.7, 62.2, 31.4, 30.6, 29.2, 27.5, 25.4, 22.5, 19.5, 14.0

Example 13

H NMR (CDCl$_3$, 90 MHz) δ0.93 (t, J=9.0 Hz, 3H), 1.20 (t, J=8.1 Hz, 3H), 1.82~2.30 (m, 6H), 3.95 (q, J=8.1 Hz, 2H), 4.95~5.43 (m, 2H)

What is claimed is:

1. A method for preparing a cis-olefin of the following general formula (2):

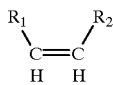
(2)

wherein R$_1$ and R$_2$ are independently selected from the group consisting of (1) an ester group, (2) substituted silyl group, (3) carboxyl group, (4) cyano group, (5) aliphatic hydrocarbon group having 1 to 20 carbon atoms unsubstituted or substituted with at least one ester group or unprotected or protected hydroxy group with at least one substituted silyl group, alkoxyalkyl group, acyl group, trityl group, tetrahydropyranyl group, benzyl group or p-chlorobenzyl group, and (6) phenyl group unsubstituted or substituted with at least one hydroxy group, with a proviso that R$_1$ and R$_2$ are not simultaneously unsubstituted aliphatic hydrocarbon groups or phenyl groups, said method comprising the steps of forming a mixture comprising formic acid, triethylamine, n-tributylphosphine, and tris (dibenzylideneacetone) dipalladium (0)-chloroform adduct (Pd$_2$(DBA)$_3$CHCl$_3$) in a solvent, and subsequently adding thereto an alkyne of the following general formula (1):

(1)

wherein R$_1$ and R$_2$ are as defined above, under effective reduction conditions,
wherein said formic acid is present in said mixture in a molar amount greater than the molar amount of the alkyne up to about 1000 mol % based on the amount of the alkyne and the palladium complex catalyst is present in an amount of about 0.1 to 100 mol % based on the amount of the alkyne.

2. The method of claim 1, wherein said R$_1$ and R$_2$ are independently selected from the group consisting of an ester group, a carboxyl group, an aliphatic hydrocarbon group having 1 to 20 carbon atoms unsubstituted or substituted with at least one ester group or hydroxy group which hydroxy group is unprotected or is protected with at least one substituted silyl group, acyl group, or tetrahydropyranyl group, and a phenyl group which is unsubstituted or is substituted with at least one hydroxy group.

3. The method of claim 1, wherein the formic acid is present in an amount of about 150 to 1000 mol %.

4. A method for preparing a cis-olefin of the following general formula (2):

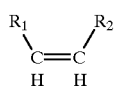
(2)

wherein R$_1$ and R$_2$ are independently selected from the group consisting of (1) an ester group, (2) substituted silyl group, (3) carboxyl group, (4) cyano group, (5) aliphatic hydrocarbon group having 1 to 20 carbon atoms unsubstituted or substituted with at least one ester group or unprotected or protected hydroxy group with at least one substituted silyl group, alkoxyalkyl group, acyl group, trityl group, tetrahydropyranyl group, benzyl group or p-chlorobenzyl group, and (6) phenyl group unsubstituted or substituted with at least one hydroxy group, with a proviso that R$_1$ and R$_2$ are not simultaneously unsubstituted aliphatic hydrocarbon groups or phenyl groups, said method comprising the steps of forming a mixture comprising formic acid, triethylamine, n-tributylphosphine, and tris (dibenzylideneacetone) dipalladium (0)-chloroform adduct (Pd$_2$(DBA)$_3$CHCl$_3$) in a solvent, and subsequently adding thereto an alkyne of the following general formula (1):

(1)

wherein R$_1$ and R$_2$ are as defined above, under effective reduction conditions, wherein said formic acid is present in said mixture in a molar amount greater than the molar amount of the alkyne based on the amount of the alkyne and the palladium complex catalyst is present in an amount of about 0.1 to 100 mol % based on the amount of the alkyne.

5. The method of claim 4, wherein the formic acid is present in an amount of about 150 to 1000 mol %.

6. The method of claim 1, wherein the aliphatic hydrocarbon group having 1 to 20 carbon atoms does not include a double bond.

7. The method of claim 4, wherein the aliphatic hydrocarbon group having 1 to 20 carbon atoms does not include a double bond.

* * * * *